United States Patent [19]
Lavender et al.

[11] Patent Number: 5,562,107
[45] Date of Patent: Oct. 8, 1996

[54] RECLOSABLE WOUND COVER

[75] Inventors: Michael R. Lavender, Chicago; David D. Rhodes, Cary, both of Ill.

[73] Assignee: Hollister Incorporated, Libertyville, Ill.

[21] Appl. No.: 534,273

[22] Filed: Sep. 27, 1995

[51] Int. Cl.$^6$ .............................. A61F 13/00; A61F 5/00
[52] U.S. Cl. ............................... 128/888; 602/41
[58] Field of Search .................... 128/846, 888, 128/889; 602/41, 42, 52

[56] References Cited

U.S. PATENT DOCUMENTS

| Re. 29,319 | 7/1977 | Nordby et al. | 128/275 |
|---|---|---|---|
| 679,918 | 8/1901 | Shears . | |
| 697,637 | 4/1902 | Lee . | |
| 720,812 | 2/1903 | Johnson . | |
| 2,367,690 | 1/1945 | Purdy | 128/888 |
| 3,556,096 | 1/1971 | Fuller | 128/888 |
| 3,954,105 | 5/1976 | Nordby et al. | 128/275 |
| 4,250,882 | 2/1981 | Adair | 128/275 |
| 4,341,208 | 7/1982 | Gordon | 128/156 |
| 4,399,816 | 8/1983 | Spangler | 128/888 |
| 4,468,227 | 8/1984 | Jensen | 604/327 |
| 4,477,325 | 10/1984 | Osburn | 204/159.12 |
| 4,641,643 | 2/1987 | Greer | 128/888 |
| 4,738,257 | 4/1988 | Meyer et al. | 128/156 |
| 4,795,435 | 1/1989 | Steer | 604/355 |
| 4,917,112 | 4/1990 | Kalt | 128/156 |
| 5,092,323 | 3/1992 | Riedel et al. | 602/54 |
| 5,395,675 | 3/1995 | Altholz et al. | 428/195 |
| 5,497,788 | 3/1996 | Inman | 128/888 |

FOREIGN PATENT DOCUMENTS

| 701472 | 3/1931 | France . |
|---|---|---|
| 288220 | 2/1929 | United Kingdom . |

*Primary Examiner*—Michael A. Brown
*Attorney, Agent, or Firm*—Tilton, Fallon, Lungmus

[57] ABSTRACT

A reclosable wound cover having a base for securement to the skin surfaces of a patient surrounding a wound and having a reclosable, transparent cover is disclosed. The base is formed of a barrier layer of soft, conformable fluid-absorbing, adhesive material and a thin, elastomeric backing layer which covers a surface of the barrier layer opposite from its skin-contacting surface. The cover includes a planar, transparent cover film which allows for visual inspection of the underlying wound through an opening in the base. The cover is smaller than the perimeter of the base so that lifting forces applied to the cover will not tend to separate the base from the skin surfaces of the patient and so that the cover does not contact the skin surfaces of the patient. An adhesive border is secured along the peripheral edge of the cover for releasably securing it to the backing layer of the base. Adhesive border has a greater affinity for remaining secured to the cover film and to the backing layer of the base and may take the form of an opaque strip of double-sided adhesive tape. A hinge is provided along one linear edge of the perimeter of the cover film for guiding the cover between an open position and a closed position in which the perimeter of the cover film lies within the perimeter of the base and the adhesive border is secured to the backing layer of the base.

19 Claims, 3 Drawing Sheets

RECLOSABLE WOUND COVER

BACKGROUND AND SUMMARY

Full-thickness dermal wounds often extend through the subcutaneous layer and are typically treated by packing the wound with dressing material to absorb wound exudate, reduce pain and prevent bacterial proliferation. Currently, such wound packings are retained in the wound by adhesive-backed tapes or films which are applied over the wound and adhesively secured to the skin surfaces surrounding the wound. When access to the wound is required for visual inspection, changing of the packing, or other reasons, the adhesive tape or film must be removed from the skin in order to expose the wound. Since many wounds require frequent visual inspection about every three to four hours and packings are often changed on average three times a day, the repeated stripping and application of an adhesive tape or covering to the wound site can cause significant skin irritation and even stripping of the skin.

In addition to the problems encountered with patient discomfort, the application of a new adhesive tape or covering every time the wound is inspected or the packing is changed is an extremely time-consuming process. The adhesive tape or covering must be carefully cut to size each time to ensure that the wound margins are avoided since application of adhesive to the wound itself could be intensely painful to the patient and detrimental to wound healing upon removal. The adhesive tape or covering must also be modified to be compatible with the location of the wound and accommodate for the curvature of the skin, skin folds, other wounds, other medical devices, etc. In addition, because adhesive-backed films, especially polyurethane dressings, are relatively expensive products, frequent changing and discarding of such dressings several times a day can be cost prohibitive.

Wound covers having a base portion which is secured to the skin surfaces surrounding a wound and having a reclosable cover are well known and examples of such devices are disclosed in U.S. Pat. Nos. 5,395,675, 4,795,435, 4,468,227 and RE. 29,319. However, it is believed that many of these constructions suffer from one or more shortcomings which make the devices less than effective in providing a reclosable wound cover which facilitates frequent opening and closing of the cover for frequent access to the wound. One such shortcoming lies in the fact that the upper layers of the base or the covers of such devices are generally larger than the adhesive which secures the device to the skin surfaces surrounding the wound. It is believed that repeated manipulation and opening and closing such large, and sometimes bulky, covers can adversely affect the adhesive attachment between the base and the skin surfaces surrounding the wound. Another shortcoming lies in the fact that many of such devices rely upon acrylic adhesives, either solely or in part, to adequately secure the device to the patient rather than more skin-friendly skin barrier materials.

An important aspect of this invention therefore lies in providing a reclosable wound cover which relies entirely on a skin barrier material for effective long-term attachment to the skin surfaces of the patient while still allowing for frequent opening and closing of the cover for inspection or access to the wound without affecting the attachment of the skin barrier material to the patient. The cover includes a planar, transparent cover film which permits visual inspection of the wound through an opening in the base. The cover also includes an adhesive border for releasably securing the cover to a backing layer of the base, and the cover film and backing layer of the base are formed of dissimilar materials so that the adhesive border has a greater affinity for remaining secured to the cover film than to the backing layer of the base. The cover is also smaller in outline than the base so that lifting forces applied to the cover will not tend to peel the larger base away from the skin surfaces of the patient and so that the cover, when it is re-closed, will always seal against the film of the base and not against the skin. The skin-friendly nature of the barrier layer allows the base to remain secured to the skin surfaces surrounding the wound for relatively long periods of time while the transparent cover allows for visual inspection and frequent access to the wound by opening and closing the cover.

Briefly, the reclosable wound cover of this invention comprises a base including a barrier layer of soft, conformable fluid-absorbing adhesive material and a thin, elastomeric backing layer covering a surface of the barrier layer opposite from its skin-contacting surface. The barrier layer and backing layer are coplanar and have a co-extensive perimeter so that the base is secured to the skin surfaces of the patient entirely by the barrier material. The wound cover also includes a reclosable cover having a planar, transparent cover film having a peripheral edge defining a perimeter smaller than the perimeter of the base. An adhesive border is secured along the peripheral edge of the cover film for releasably securing the cover to the backing layer of the base. The adhesive border has a greater affinity for remaining secured to the cover film than to the backing layer of the base so that the adhesive remains on the cover film during repeated opening and closing of the cover. Hinge means are secured along one end of the perimeter of the cover and to the backing layer for guiding the cover between an open position and a closed position in which the perimeter of the cover lies within the perimeter of the base and the adhesive border is secured to the backing layer of the base.

It is important that the perimeter of the cover is smaller than the perimeter of the base so that lifting forces applied to the cover will not tend to pull the larger barrier layer away from the surface of the skin and so that the cover does not extend beyond the base and contact the skin surfaces. Since the adhesive border will generally be composed of one type of adhesive, the cover film and the backing layer of the base are preferably composed of dissimilar materials so that the adhesive will have a greater affinity for remaining attached to the cover film than to the backing layer. In a preferred embodiment, the cover film is composed of polyurethane while the backing film is composed of a highly stretchable, gas and moisture vapor permeable polyetheramide, such as MEDIFILM sold by Bertek, Inc. of Saint Albans, Vt. Such a construction is believed to be particularly effective since the MEDIFILM adheres particularly tenaciously to the barrier material so that repeated opening and closing of the cover will not cause the backing film or layer to delaminate from the barrier material.

To further facilitate repeated opening and closing of the cover, the cover preferably includes at least one lift tab having a non-adhesive undersurface so that it will not adhere to the base. The user can readily lift and grip the tab to initiate and facilitate opening of the cover. The cover may also include tapered portions which extend from the opposite edges of the cover and converge towards the lift tab so that lifting forces exerted on the cover will be minimal at first and then will progressively increase as the tapered portions and cover are pulled back off of the base.

In one embodiment, the hinge means comprises a hinge composed of a layer of polymeric film having a layer of pressure-sensitive adhesive along its undersurface. The pressure-sensitive adhesive is preferably of moderate tack and is formulated to function in the presence of moisture. The hinge preferably extends along substantially one linear edge of the cover so that, during the reclosing operation, the hinge guides the cover back to a closed position within the perimeter of the base, thereby avoiding contact between the adhesive border of the cover and the skin surfaces of the patient.

In the preferred embodiment, the adhesive border takes the form of a peripheral strip of double-sided adhesive tape having first and second adhesive layers and a relatively non-stretchable substrate interposed between the adhesive layers. The substrate is preferably opaque and forms a visible frame about the peripheral edge of the cover film to visually assist the user in manipulating the transparent cover film. The increased thickness of the double-sided adhesive tape also physically assists the user in manipulating the thin cover film.

The base and cover of the wound cover may take the form of various shapes and sizes depending upon the particular application for which it is intended. In one alternate embodiment, the base and cover have a generally elongated, rectangular shape and the cover is provided with two lift tabs for facilitating repeated opening and closing of the cover.

Other objects, features and advantages of the present invention will become apparent from the specification and drawings.

DETAILED DESCRIPTION OF PREFERRED EMBODIMENTS

Figure 1:
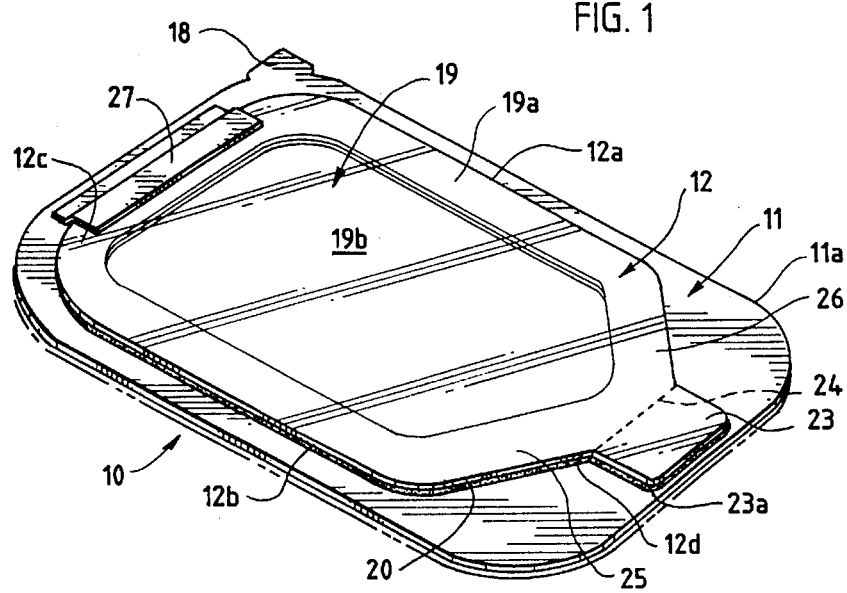
FIG. 1 is a perspective view of a reclosable wound cover embodying the invention.

Referring to the drawings, the numeral 10 generally designates a reclosable wound cover having a base 11 for securement to the skin surfaces of a patient surrounding a wound and a reclosable cover 12. Base 11 is shown in the form of a generally rectangular pad having rounded corners. However, it will be understood that the configuration and size of the wound cover may vary considerably depending upon the particular use for which it is intended.

Figure 2:
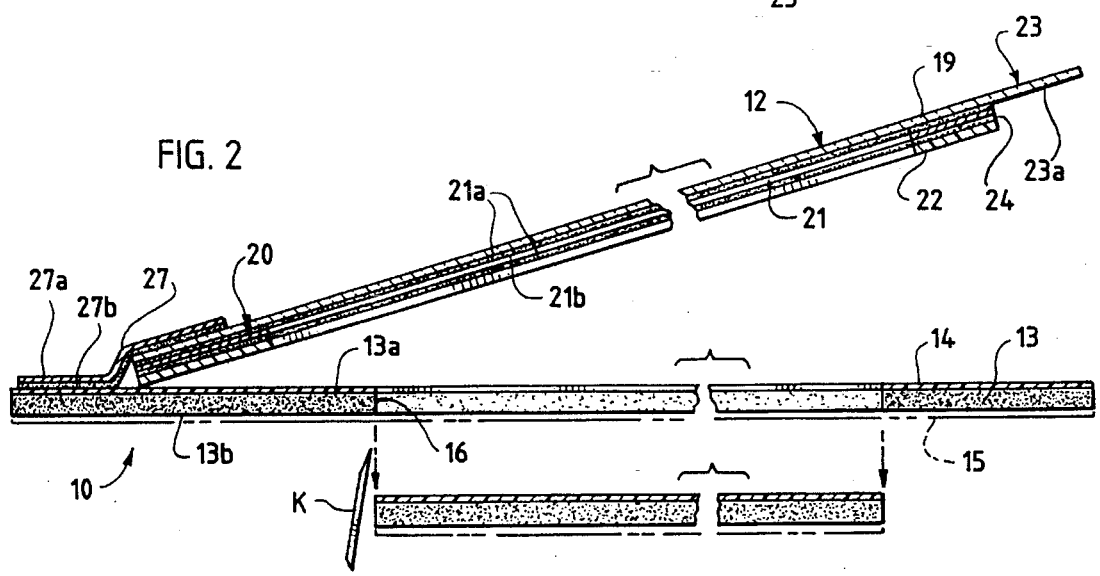
FIG. 2 is a side, somewhat enlarged cross-sectional view of the wound cover shown in FIG. 1.

As shown most clearly in FIG. 2, base 11 is generally composed of three layers: a barrier layer 13, a backing layer 14, and a removable release sheet 15 (shown in phantom). Barrier layer 13 is composed of a soft, conformable, fluid-absorbing adhesive material having both wet and dry tack. While various materials, all commonly known as "skin barrier" materials, may be used, particularly effective results have been obtained utilizing a skin barrier material formulated from a mixture of elastomers and hydrocolloids as described in co-owned U.S. Pat. Nos. 4,477,325 and 4,738,257. In such a composition, polyisobutylene is employed as one elastomeric ingredient blended with a cross-linking elastomeric resin. Cross-linkable resins which blend with polyisobutylene to form a continuous elastomeric phase include the copolymer resins formed from ethylene and vinyl acetate (EVA resins). The EVA copolymers may also be cross-linked by gamma irradiation. While Pat. Nos. 4,447,325 and 4,738,257 are believed to disclose preferred compositions for forming barrier layer 13, it will be understood that other skin barrier materials having somewhat similar properties are known and may be used.

When applied to a patient, the skin-contacting surface 13b of barrier layer 13 adheres to the skin surfaces surrounding the wound and secures wound cover 10 to the patient. To protect the tacky skin-contacting surface 13b prior to application, that surface is normally covered by release sheet 15 (shown in phantom) which can be formed of paper, plastic film, or any other suitable material having its upper surface coated with a release agent such as silicone. Prior to application, release sheet 15 may be readily peeled away from the skin-contacting surface of the barrier layer to permit adhesive application of the cover to the patient.

The surface 13a of barrier layer 13 opposite from the skin-contacting surface is covered by backing layer 14. Backing layer 14 and barrier layer 13 are coplanar and have a coextensive base perimeter 11a so that only surface 13b of the barrier layer contacts and secures the cover to the patient when in use. Backing layer 14 is composed of a thin, elastomeric film formed of any of a number of gas and moisture vapor permeable polymeric materials. The film should be occlusive with respect to particulates, bacteria and liquid water; however, it should be capable of transmitting both moisture vapor and gases such as oxygen and carbon dioxide. The film should also be easily stretchable to accommodate and provide minimal resistance to expansion of the barrier layer 13 when that layer absorbs fluid and swells in use. To allow viewing of the underlying barrier layer, the film is also preferably translucent.

Thermoplastic films having such characteristics are known in the medical field. In the preferred embodiment, backing layer 14 is composed of such a polyetheramide film sold under the designation "MEDIFILM" by Bertek, Inc. of Saint Albans, Vt. It has been found that such a film adheres particularly tenaciously to the skin barrier layer and resists delamination during repeated opening and closing of cover 12. Other suitable films include various polyesters such as the copolymers of various cyclic polyesters and one such film is sold under the name HYTREL by DuPont. However, it will be understood that other suitable films having similar properties may also be used.

Figure 4:
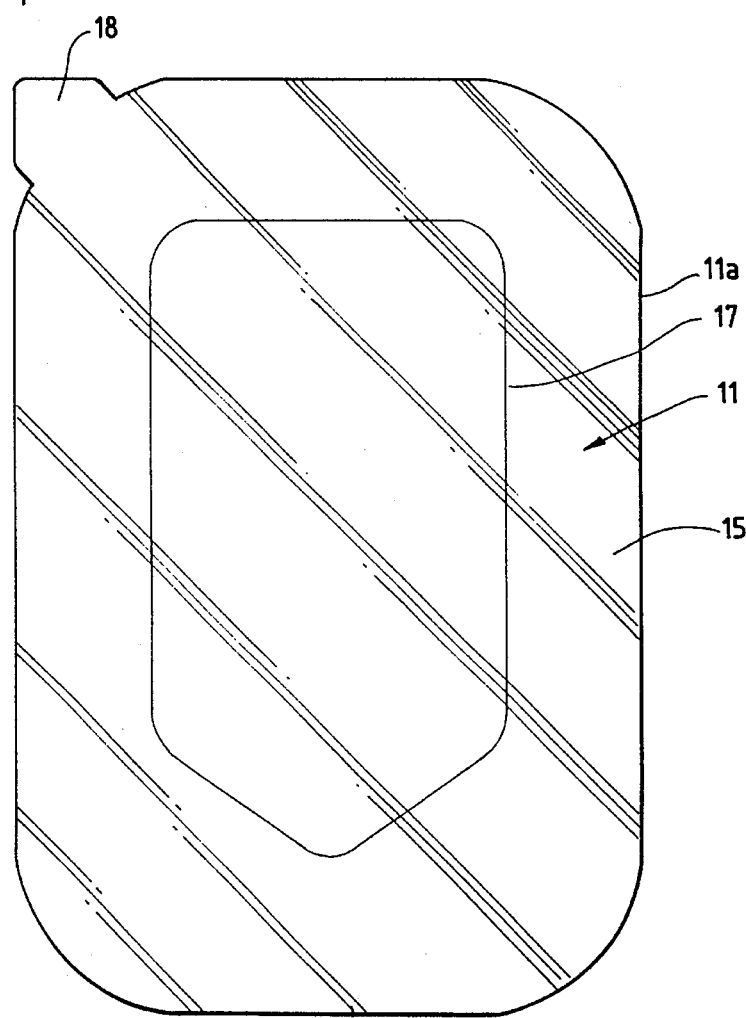
FIG. 4 is a bottom plan view of the reclosable wound cover embodying the invention.
Figure 5:
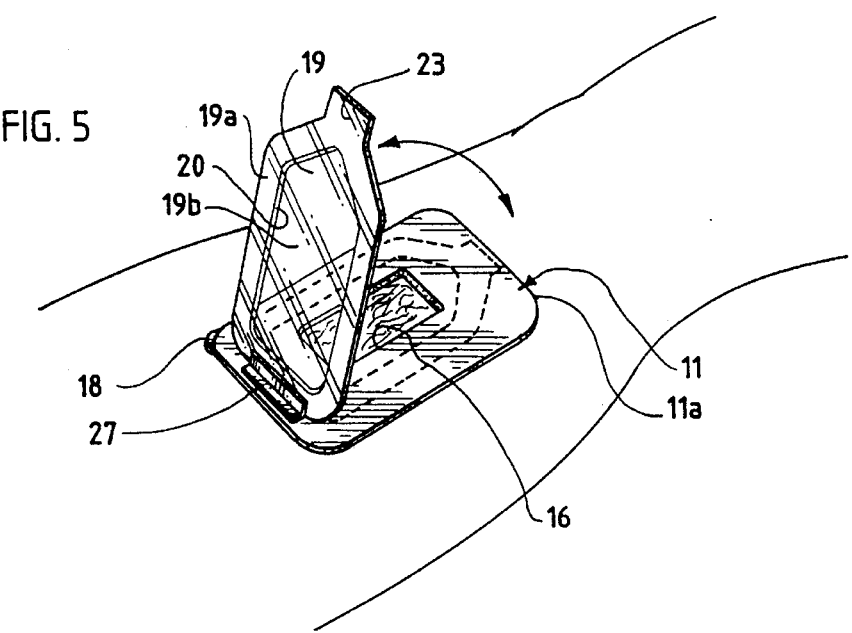
FIG. 5 is a perspective view illustrating the reclosable wound cover secured to a patient.

Prior to removal of release sheet 15 and application of wound cover 10 to the patient, the user cuts an opening 16 in base 11 such as with a knife K, or other suitable instrument, as shown in FIG. 2. Opening 16 should be sized slightly larger than the margins of the wound and care should be taken so that the barrier layer does not directly contact the wound, which could be painful to the patient and detrimental to wound healing upon removal. As shown in FIG. 4, the underside of release sheet 15 includes a borderline 17 for indicating the largest opening which may be cut in base 11 without affecting the adhesive border that secures cover 12 to base 11. As shown in FIG. 5, opening 16 allows for wound inspection or packing replacement without removing adhesive barrier layer 13 or base 11 from the surfaces of the skin. The skin-friendly nature of the barrier layer allows it to be used for relatively long-term application for periods of up to approximately 4 days, and the opening 16 allows the wound to be frequently accessed several times a day without removing the base from the skin surfaces surrounding the wound.

As shown most clearly in FIGS. 1, and 4–6, base 11 may include a tab 18 at one of its corners for facilitating removal of base 11 from the skin surfaces of the patient. Due to its relatively small surface area, tab 18 can be easily separated from the skin surfaces and used as a gripping means to initiate and facilitate removal of the remainder of base 11 from the skin surfaces of the patient.

Cover 12 is generally composed of two main components; a planar, transparent cover film 19 and a relatively non-stretchable adhesive border 20. Cover film 19 may be composed of any of a number of suitable transparent polymeric films which allow visual inspection of an underlying wound and should also be permeable to gases such as oxygen. One suitable film for forming cover film 19 is polyurethane which is generally stretchable, but other films having similar properties may also be used. However, it is important that the material of cover film 19 be dissimilar from the material of backing film 14 as will be described in more detail below.

Adhesive border 20 is secured to and extends along the peripheral edge or perimeter 19a of cover film 19 for releasably securing cover film 19 to backing layer 14 of base 11. Adhesive border 20 is provided only along the periphery of the cover film and forms a frame which surrounds a central transparent viewing area 19b of the film through which opening 16 in base 11 and the underlying wound can be viewed. In the embodiment given in the illustrations, adhesive border 20 is composed of a peripheral strip of double-sided adhesive tape 21 having first and second adhesive layers 21a and a relatively non-stretchable substrate 21b interposed between the adhesive layers. The relatively non-stretchable nature of the adhesive border contributes to its being easily rolled back into a closed condition upon the base and facilitates opening of the cover since it will not generally stretch in response to lifting forces. The substrate 21b is also opaque, and preferably white, to assist the user in visually locating the margins of transparent cover film 19 during the opening and closing operation as shown in FIG. 5. The increased thickness of the double-sided tape also assists the user in physically manipulating the relatively thin cover film during the opening and closing operation. One suitable double-sided adhesive tape for forming adhesive border 20 is sold under the designation #1509 by 3M of Minneapolis, Minn. However, adhesive border 20 may take the form of other double-sided adhesive tapes or may take the form of a single layer of pressure-sensitive adhesive, such as a suitable medical grade acrylic adhesive or the like.

To protect the tacky surface of adhesive border 20 prior to use, a peripheral release sheet 22 normally extends over adhesive border 20. Release sheet 22 may be readily removed once base 11 is secured to the patient for exposing adhesive border 20 for sealing engagement with the base. Since such release sheets are well known in the medical field, it is believed that further description of release sheet 22 is not required.

Adhesive border 20 has a greater affinity for remaining secured to cover film 19 than to backing layer 14 of the base so that the adhesive will remain on the cover film during repeated opening and closing of the cover. To achieve such results, cover film 19 and backing layer 14 should be made of dissimilar materials since generally only one type of adhesive would be used in adhesive border 20. In the previously discussed preferred embodiment, cover film 19 is formed of polyurethane while backing layer 14 is formed of a stretchable polyetheramide such as MEDIFILM. In such a construction, adhesive border 20 has a greater affinity for remaining secured to the polyurethane cover film rather than to the MEDIFILM backing layer, and adhesive border 20 therefore remains secured to the cover film during repeated opening and closing of the cover. However, it will be understood that the cover film and backing layer may be composed of other suitable, dissimilar materials.

It is also important that cover 12 be constructed so that it may be repeatedly opened and re-sealed against base 11 without adversely affecting the adhesive attraction between each of (1) backing layer 14 and barrier layer 13 of the base and (2) the barrier layer 13 of the base and the skin surfaces surrounding the wound. To achieve such results, the perimeter 19a of cover film 19 is smaller in outline than the perimeter 11a of base 11 so that lifting forces applied to cover 12 will not tend to peel the larger base away from the skin surfaces. The material of the backing layer, such as MEDIFILM, is also preferably selected so that it adheres particularly tenaciously to the barrier layer to prevent delamination. The narrow width of adhesive border 20 also ensures that only minimal lifting forces are required to open cover 12.

Figure 3:
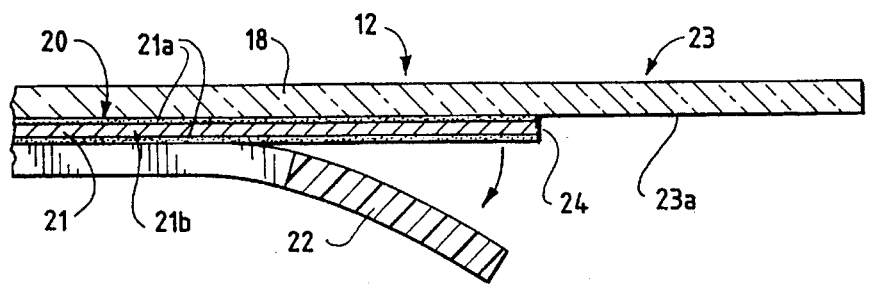
FIG. 3 is an enlarged side cross-sectional view of the pull tab of the wound cover embodying this invention.

To further facilitate easy separation of cover 12 from base 11, cover 12 includes a tab 23 having a non-adhesive or adhesive free underside 23a which will not stick to the base. Tab 23 may therefore be easily lifted off of the base and be used to initiate and facilitate separation of the remainder of cover 12 from the base. As most clearly shown in FIGS. 2 and 3, the adhesive border terminates at an edge 24 prior to tab 23 so that its underside 23a remains adhesive free. However, it will be understood that the adhesive could alternatively extend along the underside of the tab and have a release sheet section or the like adhered to it to render it non-adhesive.

In the embodiment given in FIGS. 1–5, cover 12 includes a pair of opposite longitudinal edges 12a and 12b and a pair of opposite ends 12c and 12d. End 12d of the cover includes a pair of tapered portions 25 and 26 which extend from edges 12a and 12b and converge or taper towards lift tab 23. Tapered portions 25 and 26 ensure that only minimal lifting forces will be required at first to initiate separation of cover 12 from base 11 when tab 23 is lifted and pulled back. The required lifting forces will then progressively increase as cover 12 is peeled back from base 11. Since only minimal lifting forces are required at first, the user need not exert an overly strong initial tug or pull on tab 23 in order to initiate opening of the cover. Rather, the user can lift tab 23 and then gradually increase the amount of lifting force as the cover 12 is slowly peeled back off of the base.

Hinge means are secured along the other end 12c of the cover and to backing layer 14 of base 11 for guiding the cover between an open position as shown in FIG. 5 and a closed position as indicated by broken lines in that drawing. In the embodiment given in the illustrations, the hinge means take the form of a hinge 27 which is composed of a strip of polymeric film 27a and an underlying adhesive layer 27b. Polymeric film 27a is preferably a thermoplastic polyetheramide but other suitable polymeric films may also be used. The adhesive 27b along the underside of film 27a can be any one of a number of well known pressure-sensitive adhesives. However, the adhesive is preferably of moderate tack and formulated to function in the presence of moisture. One such suitable film and adhesive combination is sold under the designation 3M 1516 POLYESTERFILM by 3M.

Hinge 27 is relatively wide and extends substantially along the linear edge of end 12c of the cover so that it guides cover 12 between an open position and a closed position in which the perimeter of cover 12 lies within the perimeter 11a of base 11. By guiding the cover back into the closed position on the base, the hinge helps to prevent inadvertent contact between the cover and the skin surfaces of the patient. It is important that cover 12 and adhesive border 20 do not extend beyond the perimeter 11a of the base during the opening and closing operation since contact between adhesive border 20 and the skin surfaces of the patient could contaminate that adhesive and require premature disposal of the wound cover.

Figure 6:
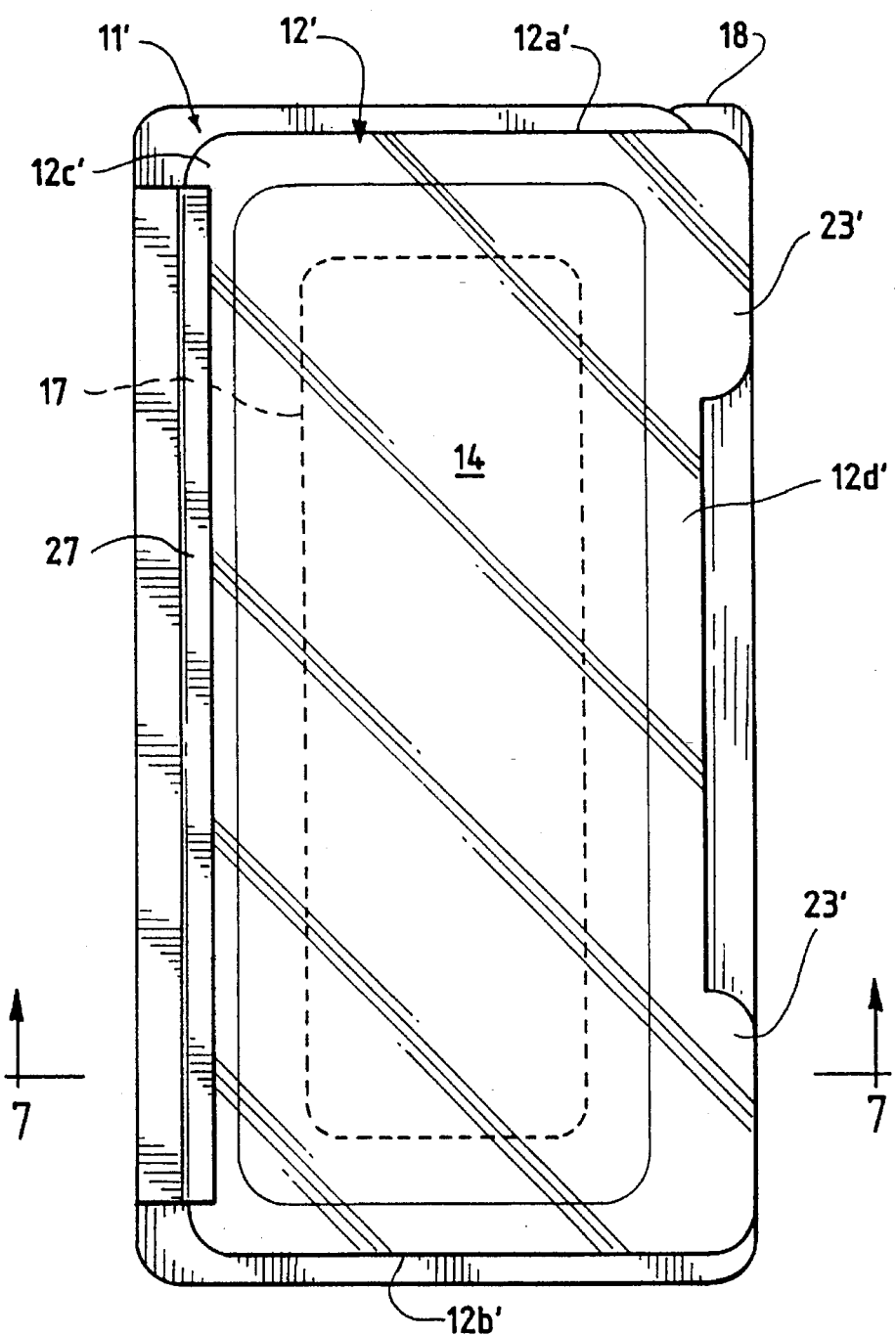
FIG. 6 is a top plan view of an alternate embodiment of a reclosable wound cover embodying the invention.
Figure 7:
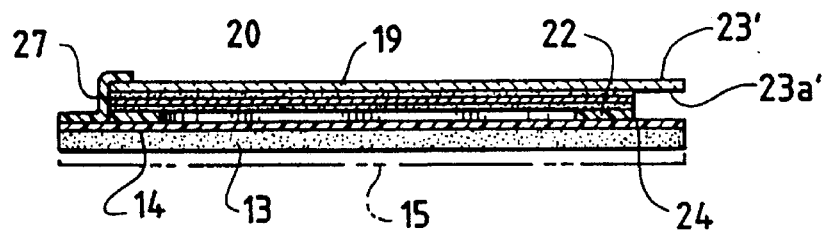
FIG. 7 is a side, somewhat enlarged cross-sectional view of the embodiment of the wound cover shown in FIG. 6.

In an alternate embodiment shown in FIGS. 6 and 7, the reclosable wound cover is substantially the same in construction and operation as previously described except for the size and shape of base 11' and cover 12'. Base 11' and cover 12' generally have an elongated rectangular shape and one end 12c' of the cover is secured to the base by hinge 27. The opposite end 12d' of the cover is linear and includes a pair of lift tabs 23' which are each adjacent to the opposite edges 12a' and 12b' of the cover, respectively. The two lift tabs 23' facilitate opening larger covers such as cover 12' by providing two points for initiating separation and gripping the cover during the opening operation.

While in the foregoing embodiments of the invention have been disclosed in considerable detail for purposes of illustration, it will be understood by those skilled in the art that many of these details may be varied without departing from the spirit and scope of the invention.

We claim:

1. A reclosable wound cover comprising:

a base including a barrier layer of soft, conformable fluid-absorbing, adhesive material having a skin-contacting surface, and a thin, elastomeric backing layer covering a surface of said barrier layer opposite from said skin-contacting surface and being permeable to gas and moisture vapor, said barrier layer and said backing layer being coplanar and having a coextensive base perimeter;

a reclosable cover including a planar, transparent cover film having a peripheral edge defining a perimeter smaller than said base perimeter;

an adhesive border secured along said peripheral edge of said cover film for releasably securing said cover to said backing layer of said base, said adhesive border having a greater affinity for remaining secured to said cover film than to said backing layer of said base; and hinge means secured along one end of said cover film and to said backing layer for guiding said cover between an open position and closed position in which said perimeter of said cover film lies within said perimeter of said base and said adhesive border is secured to said backing layer of said base.

2. The wound cover of claim 1 in which said adhesive border is composed of double-sided adhesive tape having first and second adhesive layers and a relatively non-stretchable substrate interposed between said adhesive layers.

3. The wound cover of claim 2 in which said substrate of said double-sided adhesive tape is opaque and forms a visible frame about the peripheral edge of said cover film and surrounds a central transparent viewing area of said cover film.

4. The wound cover of claim 3 in which said substrate is white.

5. The wound cover of claim 1 in which said adhesive border is composed of a layer of pressure-sensitive adhesive.

6. The wound cover of claim 1 in which said cover film is composed of a material dissimilar from the material of said backing layer of said base.

7. The wound cover of claim 6 in which said cover film is composed of polyurethane and said backing film is composed of polyetheramide.

8. The wound cover of claim 6 in which said cover film is composed of polyurethane and said backing film is composed of polyester.

9. The wound cover of claim 1 in which said backing film of said base is translucent.

10. The wound cover of claim 1 in which said cover includes at least one lift tab having a non-adhesive underside.

11. The wound cover of claim 10 in which the other end of said cover includes tapered portions which extend from opposite edges of said cover and converge towards said lift tab.

12. The wound cover of claim 10 in which a peripheral release sheet covers said adhesive border.

13. The wound cover of claim 1 in which said hinge means comprises a hinge composed of a layer of a polymeric film and a layer of pressure-sensitive adhesive.

14. The wound cover of claim 13 in which said pressure-sensitive adhesive is formulated to function in the presence of moisture.

15. The wound cover of claim 13 in which said hinge extends substantially along one linear edge of the perimeter of said cover.

16. The wound cover of claim 1 in which said cover includes first and second lift tabs having non-adhesive undersides and said first tab is positioned adjacent to one edge of said cover and said second lift tab is positioned adjacent to the other opposite edge of said cover.

17. The wound cover of claim 1 in which said base includes at least one corner having an extended tab for facilitating removal of said base from the skin surfaces of a patient.

18. The wound cover of claim 1 in which a release sheet extends along said skin-contacting surface of said barrier layer of said base.

19. The wound cover of claim 18 in which said release sheet includes an underside having a borderline printed thereon for indicating the location of said adhesive border of said cover.

* * * * *